United States Patent [19]

Millauer

[11] Patent Number: 4,466,926

[45] Date of Patent: Aug. 21, 1984

[54] PROCESS FOR THE PREPARATION OF α,ω-BIS-FLUOROSULFATOPERFLUOROALKANES, AND A FEW SPECIAL REPRESENTATIVES OF THESE COMPOUNDS

[75] Inventor: Hans Millauer, Eschborn, Fed. Rep. of Germany

[73] Assignee: Hoechst Aktiengesellschaft, Frankfurt am Main, Fed. Rep. of Germany

[21] Appl. No.: 398,119

[22] Filed: Jul. 14, 1982

[30] Foreign Application Priority Data

Jul. 16, 1981 [DE] Fed. Rep. of Germany ....... 3128118

[51] Int. Cl.$^3$ ............................................ C07C 141/10
[52] U.S. Cl. ................... 260/458 F; 560/180; 560/184; 204/59 F; 204/72; 204/79
[58] Field of Search ................... 260/458 F; 204/59 F, 204/72, 79

[56] References Cited

U.S. PATENT DOCUMENTS 4,235,804 11/1980 Krespan ......................... 260/458 F

OTHER PUBLICATIONS

Shreeve et al., JACS, 83, 4521 (1961).
Krespan, J. Fluorine Chem. 2, 173–180 (1972/73).
Germain et al., Tetrahedron 37, 487–491 (1981).
Lustig et al., Inorganic Chem. 3, 287–288 (1964).
Chem. Abstr. 93, 238771x (1980).

*Primary Examiner*—Nicky Chan
*Attorney, Agent, or Firm*—Curtis, Morris & Safford

[57] ABSTRACT

A method for making alpha,omega-bis-fluorosulfatoperfluoroalkanes by reacting a perfluorinated alpha-olefin with peroxodisulfuryl difluoride in the liquid phase, and compounds of the formula $$FSO_2\text{-}O\text{-}(CF_2\text{-}CF_2)_n\text{-}O\text{-}SO_2F,$$

useful as intermediates in making polymers.

11 Claims, No Drawings

PROCESS FOR THE PREPARATION OF α,ω-BIS-FLUOROSULFATOPERFLUOROAL-KANES, AND A FEW SPECIAL REPRESENTATIVES OF THESE COMPOUNDS

α,ω-Bis-fluorosulfatoperfluoroalkanes are compounds of the general formula $$FSO_2-O-R_f-O-SO_2F,$$

in which $R_f$ is a perfluorinated, branched or unbranched alkylene radical.

They are valuable intermediate products in various specialized fields, in particular in the field of polymers.

If the two ends of the perfluorinated alkylene radical $-R_f-$ are each formed by a $CF_2$ group (ie. if $R_f$ is $CF_2- \ldots -CF_2$), polymers or structural units for polymers are obtained—starting from suitable α,ω-bis-fluorosulfatoperfluoroalkanes of this type—by the following route.

The two fluorosulfato groups are first split off—say by decomposition in the presence of cesium fluoride CsF as catalyst [cf. J. Fluorine Chemistry 16 (1980), pages 63 to 73, in particular page 65, paragraph 2]— from the α,ω-bis-fluorosulfatoperfluoroalkanes, with the formation of two acid fluoride groups:

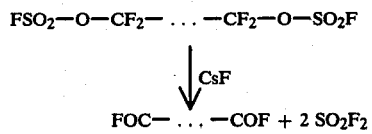

The perfluoroalkane-α,ω-dicarboxylic acid difluorides thus formed can then be used, as such or after conversion into the corresponding free dicarboxylic acids or their esters, as monomers for the preparation of polyesters or polyamides which have use properties which are of industrial interest.

The perfluoroalkane-α,ω-dicarboxylic acid difluorides can, however, only be esterified at one end, which can be effected, say, by the process described in German Offenlegungsschrift No. 2,751,050. However, this process takes place with only a low selectivity, or none at all, to give the perfluorinated dicarboxylic acid fluoride-esters, but always results in mixtures containing the starting materials, which are difficult to separate, and also diesters. The dicarboxylic acid fluoride-esters can then (after being separated by a fairly involved process) be converted by known methods, say in accordance with the following scheme of reactions, into perfluorinated vinyl ethers which still contain one ester group:

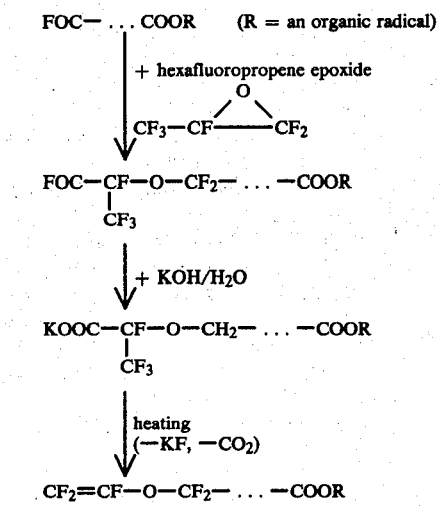

The perfluorinated vinyl ethers which still contain an ester group are important monomers for polymerization or copolymerization with other fluoroolefins (such as, for example, tetrafluoroethylene) for the purpose of producing ion-selective membranes, cation exchange compositions and fluorocarbon elastomers.

A perfluorinated dicarboxylic acid which is particularly important as a structural unit or starting substance for polymers is perfluorosuccinic acid or its difluoride or fluoride-ester. The fluorosulfato precursor of perfluorosuccinic acid and the derivatives thereof mentioned is 1,4-bis-fluorosulfatoperfluorobutane:

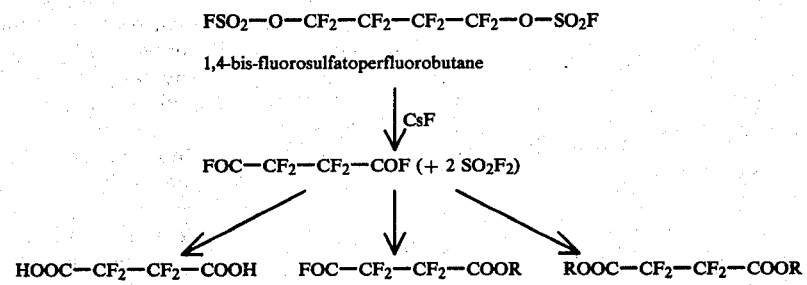

1,4-bis-fluorosulfatoperfluorobutane is, therefore, also particularly important amongst the α,ω-bis-fluorosulfatoperfluoroalkanes.

Various methods are known for the preparation of α,ω-bis-fluorosulfatoperfluoroalkanes.

One method for the preparation of, say, 1,2-bis-fluorosulfatotetrafluoroethane is described by J. M. Schreeve and G. H. Cady in J. Am. Chem. Soc. 83, 4,521 et seq., in particular 4,523 (1961). This method consists in reacting tetrafluoroethylene with peroxodisulfuryl difluoride, apparently only in the gas phase:

$$CF_2=CF_2+FSO_2-O-O-SO_2F \rightarrow$$
$$FSO_2-O-CF_2-CF_2-O-SO_2F$$

The authors refer particularly to the fact that the reaction only works at low pressures and concentrations of tetrafluoroethylene and if there is an excess, which must be maintained at all times, of peroxodisulfuryl difluoride, since otherwise—i.e., for instance, at fairly high concentrations of tetrafluoroethylene—as a result of the action of peroxodisulfuryl difluoride in forming free radicals, in the main only polymerization of the tetrafluoroethylene takes place. In the description of the experimental results, 1,2-bis-fluorosulfatotetrafluoroethane is indicated as the sole reaction product—without a mention of the yield—as well as unidentified polymeric solids and fairly small quantities of carbonyl difluoride and pyrosulfuryl fluoride.

1,4-bis-fluorosulfatoperfluorobutane and the preparation thereof are known from the article by A. Germain and A. Commeyras, published in Tetrahedron, volume 37, pages 487 to 491. It is prepared by electrolysis (anodic oxidation) of 1,4-bis-iodoperfluorobutane in a mixture composed of fluorosulfonic acid and an alkali metal fluorosulfonate. The authors are of the opinion that a direct electrode process takes place, but do not exclude a simultaneous, indirect process taking place via "I+" (page 488, right-hand column).

A yield of 70% is quoted in Table 1 on page 489 of the article by A. Germain and A. Commeyras.

Although this is a relatively high yield, the process is not entirely satisfactory overall because the starting material 1,4-bis-iodoperfluorobutane is not very readily accessible. As is known, 1,4-bis-iodoperfluorobutane is formed in only a poor yield, in addition to the main product, 1,2-diiodotetrafluoroethane, when tetrafluoroethylene is reacted with iodine.

In other respects the method of A. Germain and A. Commeyras is probably also applicable to the preparation of other α,ω-bis-fluorosulfatoperfluoroalkanes (from the corresponding α,ω-bis-iodoperfluoroalkanes).

The preparation of an α,ω-bis-fluorosulfatoperfluoroalkane having a branched perfluoroalkane chain is described by C. G. Krespan in J. Fluorine Chemistry 2, pages 173 to 179 (1972/73). The olefin—in this case hexafluoropropene—is reacted with peroxidisulfuryl difluoride in a gas phase reaction (similar to that described by J. M. Schreeve and G. H. Cady, loc. cit.) at room temperature or at a temperature slightly higher than room temperature. In this reaction the 1:1 adduct 1,2-bis-fluorosulfatohexafluoropropane is stated to be formed in a yield of 63%, together with 22% of the 2:1 adduct:

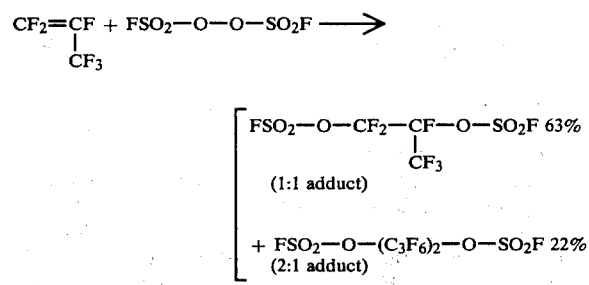

No further information is given concerning the distribution of isomers in the 2:1 adduct.

Because it is precisely the 2:1 adducts formed from perfluoroolefins and peroxodisulfuryl difluoride, in particular 1,4-bis-fluorosulfatoperfluorobutane (=the 2:1 adduct formed from tetrafluoroethylene and peroxodisulfuryl difluoride), which are of considerable importance as intermediate products for the preparation of the corresponding perfluorodicarboxylic acids and derivatives thereof and the like (see the introduction to the Description) and because the methods of synthesis available for the said 2:1 adducts have hitherto only been rather unsatisfactory, the problem has presented itself of finding an improved process for the preparation of these adducts—in particular for the preparation of 1,4-bis-fluorosulfatoperfluorobutane.

It has been possible to solve this problem, in accordance with the invention, by reacting perfluorinated α-olefins with peroxodisulfuryl difluoride in the liquid phase; however, it is necessary in this reaction to keep the concentration of the peroxodisulfuryl difluoride in the liquid phase substantially constant within a specified range of concentrations.

The invention relates, therefore, to a process for the preparation of α,ω-bis-fluorosulfatoperfluoroalkanes by reacting perfluorinated α-olefins with peroxodisulfuryl difluoride, $FSO_2O-OSO_2F$, which comprises passing the perfluorinated α-olefins into a liquid phase containing peroxodisulfuryl difluoride, the concentration of the peroxodisulfuryl difluoride in the liquid phase being kept substantially constant within the concentration range from about 0.005 to 0.2, preferably from about 0.01 to 0.1, mole/l.

The desired 2:1 adducts of perfluoroolefins and peroxodisulfuryl difluorides are formed here—in the main regardless of the process conditions within the limits indicated—in a high degree of selectivity and yield together with minor amounts of also the 1:1, 3:1, 4:1 and, in some cases, also 5:1 adducts. This result was extremely surprising, since, on the basis of the publications by J. M. Schreeve and H. Cady (loc. cit.) and of C. G. Krespan (loc. cit.), it could hardly be expected that the reaction of perfluoroolefins with peroxodisulfuryl difluoride could be influenced towards the formation of the corresponding 2:1 adducts as the main products. This is because, on the basis of the publication by J. M. Schreeve and G. H. Cady, it was necessary to assume that, because of the polymerization-initiating effect of peroxodisulfuryl difluoride, the perfluoroolefin could in any case only be reacted in a very low concentration with the peroxodisulfuryl difluoride to form an adduct—and then only to form the 1:1 adduct (1,4-bis-fluorosulfatoperfluorobutane). According to this literature reference, the formation of solid tetrafluoroethylene polymers would be expected at a fairly high concentration of perfluoroolefin.

According to the publication by C. G. Krespan, although the 2:1 adduct is also formed in addition to the 1:1 adduct, which is the main product (63%), it is only formed as a by-product (22%)—and this when using, as the starting perfluoroolefin, not tetrafluoroethylene, but hexafluoropropene.

The guiding, in accordance with the invention, of the reaction towards the 2:1 adduct as the predominant main product may well be caused by carrying out the reaction in the liquid phase (J. M. Schreeve & G. H. Cady and C. G. Krespan employed in the gas phase!) under very specific conditions of concentration.

The perfluorinated α-olefins employed for the process according to the invention are compounds of the formula $$CF_2=CF-R_f$$

in which $R_f$ denotes F or perfluoroalkyl which preferably has 1–8 C atoms, particularly preferably F or $CF_3$ and especially F. Examples of perfluorinated α-olefins of this type are tetrafluoroethylene, hexafluoropropene, octafluoro-1-n-butene, hexafluoro-1-isopentene and the like, tetrafluoroethylene and hexafluoropropene—especially tetrafluoroethylene—being particularly preferred. These perfluoroolefins can be obtained by known methods and are in some cases also commercial products.

Peroxodisulfuryl difluoride, $FSO_2-O-O-SO_2F$, can also be prepared by known processes (see F. B. Dudley, J. Chem. Soc. 1963, pages 3,407–3,411)—ie., for instance, by the direct reaction between $SO_3$ and fluorine in the presence of an $Ag_2F_2$ catalyst, by the oxidation of metal fluorosulfonates with fluorine or by the anodic oxidation of solutions of alkali metal fluorosulfonates in fluorosulfonic acid.

In carrying out the process according to the invention, the perfluoroethylene is generally passed into peroxodisulfuryl difluoride, dissolved in an inert solvent, at such a rate that, as far as possible, no perfluoroolefin, or in any case not too much thereof, remains unreacted.

Examples of inert solvents which can be used are perfluorinated hydrocarbons, fluorosulfonic acid ($FSO_3H$) and also the solutions of alkali metal fluorosulfonates in fluorosulfonic acid which are used for the electrochemical preparation of peroxodisulfuryl difluoride, and the $\alpha,\omega$-bis-fluorosulfatoperfluoroalkanes which are themselves formed in the reaction according to the invention, etc.

In principle, the reaction temperature selected can be within a fairly wide range—in general between about $-20$ and about $+100°$ C., but it is preferably between about $0°$ and $50°$ C.

Since the boiling point of peroxodisulfuryl difluoride is about $65°$ C., the reaction can, of course, only be carried out above this temperature under normal pressure if an inert solvent boiling at a correspondingly higher temperature is used.

Although, in principle, sub-atmospheric pressures or super-atmospheric pressures are possible, normal pressure is clearly preferable for economic reasons alone.

In addition to carrying out the reaction in the liquid phase, it is an essential and critical factor for the success of the reaction that the concentration of the peroxodisulfuryl difluoride in the liquid phase is kept within the concentration range indicated above—and, in turn, kept substantially constant within this range. Because peroxodisulfuryl difluoride is consumed in the course of the reaction, the latter must, therefore, be fed continuously. The control of the concentration of the peroxodisulfuryl difluoride in the liquid phase can be effected in a known manner—for instance by taking samples and titrating.

The reaction mixture can also be worked up in a known manner—for example by distillation.

The reaction can be carried out either continuously or discontinuously.

A preferred embodiment of the process according to the invention consists in passing the perfluorinated $\alpha$-olefins into the liquid phase of an electrolytic cell in which peroxodisulfuryl difluoride is formed by electrolyzing a solution of an alkali metal fluorosulfonate in fluorosulfonic acid, and in which peroxodisulfuryl difluoride is continuously supplemented at the rate at which it is consumed. In this case, the solution of alkali metal fluorosulfonate in fluorosulfonic acid is also, at the same time, the solvent for the peroxodisulfuryl difluoride, and the solution of the alkali metal fluorosulfonate and of the peroxodisulfuryl difluoride in fluorosulfonic acid constitutes the liquid phase of the process according to the invention.

It is particularly convenient and simple to carry out the process as an "in cell" process, using electrochemical cells, for instance in the form of a pot or trough, which are preferably used in the laboratory or on a fairly small industrial scale. The electrochemical cells can be divided or undivided cells. In general, an undivided cell is completely adequate. A factor against its simpler and cheaper design is, however, a slightly lower current yield, which is caused by the cathodic reduction of the peroxodisulfuryl difluoride.

In a divided cell, porous diaphragms, such as, for example, glass frits or porous tetrafluoroethylene, can be used to partition the electrode spaces.

Possible electrode materials are the anode and cathode materials which are known for the electrochemical production of peroxodisulfuryl difluoride. Examples of suitable materials are, therefore, platinum and platinum alloys (such as platinum-iridium alloys and the like). The preferred electrode material is glassy carbon.

The electrolyte is composed of fluorosulfonic acid, in which a salt—preferably an alkali metal salt—of fluorosulfonic acid has been dissolved in order to improve the electrical conductivity. Conducting salts of this type which are particularly preferred are Li, Na and K fluorosulfonates.

The electrolyte solution is advantageously prepared from an alkali metal chloride or bromide, which is dissolved in fluorosulfonic acid, in a concentration of about 0.05 to about 5M, preferably about 0.1 to about 1M. The hydrogen chloride or hydrogen bromide, thus liberated escapes from the solution and is removed completely by blowing eg nitrogen through the electrolyte solution. Electrolyte solutions prepared in this manner can be employed for the electrolysis without further pretreatment.

The perfluoroolefin is introduced into the electrolyte phase at, or preferably after, the commencement of the electrolysis—when the desired concentration of peroxodisulfuryl difluoride has been reached. In any case, if gaseous perfluoroolefins—in particular tetrafluoroethylene—are introduced, it is advisable to ensure that the gas stream is vigorously and rapidly mixed with the liquid phase. It is advisable in this connection to introduce the stream of perfluoroolefin in as finely divided a form as possible, for example by using jets or frits, and/or to agitate the electrolyte liquid by stirring or circulatory pumping.

In the event—which is preferable—that tetrafluoroethylene is used as the perfluoroolefin, the partial pressure of the latter can, in general, be about 0.1 to 10 bar, preferably about 0.3 to 3.0 bar. The tetrafluoroethylene can be fed in, if appropriate, with the addition of an inert gas, such as, for example, nitrogen, in order to produce partial pressures within the lower portion of this range. Higher partial pressures can be produced, if appropriate, by using excess pressure.

If tetrafluoroethylene is employed as the perfluoroolefin, the formation of undesirable solids can be suppressed virtually completely, for instance by adding iodine, in which connection quantities of about 10 to 100 ppm of iodine, relative to the quantity of electrolyte, are generally adequate.

If other perfluoroolefins are used, hardly any polymerization takes place during the reaction with peroxodisulfuryl difluoride.

The current densities used are generally between about 2 and 200 mA.cm$^{-2}$, preferably about 30 to 100 mA.cm$^{-2}$.

In general, the process requires no special activation or finishing operations for the electrodes and the electrolyte before the commencement of the electrolysis. The electrolysis is started by switching on the current in the electrolytic device, and the appropriate perfluoroolefin is then introduced.

This preferred embodiment of the process according to the invention can, in principle, also be put into practice either discontinuously or continuously.

In the discontinuous procedure, the electrolysis is terminated after a certain quantity of electricity has been passed—advantageously about 0.1 to 0.7 F/mole of the fluorosulfonic acid originally present in the electrolyte. Since the solubility of the α,ω-bis-fluorosulfatoperfluoroalkanes which can be obtained or are obtained in accordance with the process, in the electrolyte system used in the preferred embodiment which has been described, falls off as their chain length increases, separation, as a liquid phase, of, in particular, the reaction products which have a fairly long chain takes place from the electrolyte as the reaction proceeds.

When the electrolysis of a batch is complete, the reaction products can be isolated either by distillation or, preferably, by separating off the organofluorine phase which has separated out. The electrolyte phase obtained by the separation method is preferably re-used for a subsequent batch after being replenished with fresh fluorosulfonic acid. It is also possible to re-use the electrolyte phase several times.

The fact that the reaction product can be isolated by separation and that the electrolyte phase can be regenerated enable the process to be carried out also in a continuous manner by means of operations which are known to those skilled in the art.

The products from the process are isolated and prepared in a pure state in a manner which is known per se. After they have been removed from the electrolysis mixture, the α,ω-bis-fluorosulfatoperfluoroalkanes are, therefore, first washed once or several times with water and/or sodium bicarbonate solution, until they are neutral, in order to remove residues of electrolyte, and are dried with a non-basic drying agent, for example sodium sulfate or a molecular sieve. In this connection, it can be advantageous, before the washing process, to carry out a simple distillation under reduced pressure or a filtration of the material discharged from the electrolysis, in order to remove small quantities of solid by-products, which impede the separation of the reaction products from the washing liquids.

After being washed and dried, the reaction products are separated into their individual components by a fractional distillation, this being carried out either under atmospheric pressure or—if compounds having a fairly long chain are distilled—preferably under a reduced pressure of about 10 to 100 mbar.

Finally, it is also possible to carry out the process according to the invention in conjunction with the electrochemical preparation of the peroxodisulfuryl difluoride as an "ex cell" process, ie. to react the particular perfluoroolefin with the peroxodisulfuryl difluoride which has been formed at the anode, outside the electrochemical cell in a separate reactor connected to the latter. In this case a suitable external circulation of the electrolyte must be provided—advantageously a circulation such that a (part) stream containing peroxodisulfuryl difluoride is fed to the reactor which is coupled to the electrolytic cell, and a stream of liquid depleted in peroxodisulfuryl difluoride is recirculated back to the electrolytic cell.

In the process according to the invention, the appropriate perfluoroolefin peroxodisulfuryl difluoride 2:1 adducts are obtained in a high degree of selectivity and yield (up to about 75% of theory, relative to the starting perfluoroolefin). If tetrafluoroethylene is used as the starting perfluoroolefin, this adduct is 1,4-bis-fluorosulfatoperfluorobutane:

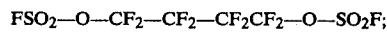
$FSO_2-O-CF_2-CF_2-CF_2CF_2-O-SO_2F$;

if hexafluoropropene is used as the starting perfluoroolefin, the 2:1 adduct is 1,4-bis-fluorosulfato-2,3-bis-(trifluoromethyl)-butane:

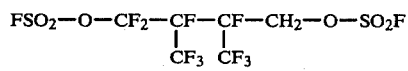
$$FSO_2-O-CF_2-\underset{CF_3}{\underset{|}{CF}}-\underset{CF_3}{\underset{|}{CF}}-CH_2-O-SO_2F$$

The isomers of this compound which are possible—at least in theory—are formed here only to a minor extent.

Correspondingly, if higher perfluorinated α-olefins are used as the starting material, the formula of the main product of the process is:

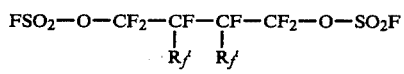
$$FSO_2-O-CF_2-\underset{R_f'}{\underset{|}{CF}}-\underset{R_f'}{\underset{|}{CF}}-CF_2-O-SO_2F$$

in which $R_f'$ is a perfluoroalkyl radical which preferably contains 2–8 C atoms.

The by-products of the process according to the invention are primarily the corresponding 1:1, 3:1, 4:1 and 5:1 adducts of the perfluoroolefin and peroxodisulfuryl difluoride. Of these, inter alia, the tetrafluoroethylene/peroxodisulfuryl difluoride adducts of the formula

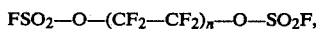
$FSO_2-O-(CF_2-CF_2)_n-O-SO_2F$, in which n is an integer from 3–5, are new compounds and are therefore also a subject of the invention—as is also the hexafluoropropene/peroxodisulfuryl difluoride 2:1 adduct mentioned above. The hexafluoropropene/peroxodisulfuryl difluoride 2:1 adduct referred to, of the structure indicated above, is not mentioned by name in the paper by C. G. Krespan (loc. cit.).

The α,ω-bis-fluorosulfatoperfluoroalkanes obtained by the process according to the invention are used in the manner described initially in a general way for compounds of this type. Additionally (and preferably) the compounds are used for the preparation of the corresponding ω-fluorosulfatoperfluoroalkanoic acid esters by the process of U.S. patent application Ser. No. 398,118 filed on even date herewith. In this process, the α,ω-bis-fluorosulfatoperfluoroalkanes are reacted in the presence of catalytic to approximately equimolar quantities of one or more alkali metal fluorides and/or alkali metal hydrogen fluorides and also in the presence of at least an equimolar quantity of an alcohol ROH (R is an alkyl radical) and, if appropriate, also in the presence of an inert solvent which does not dissolve the alkali metal fluorides and/or alkali metal hydrogen fluorides (eg methylene chloride). Using 1,4-bis-fluorosulfatoperfluorobutane as an example, this reaction may be set out as follows:

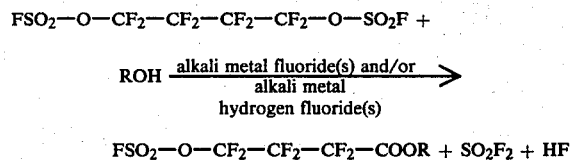

The ω-fluorosulfatoperfluoroalkanoic acid esters can then be processed further, for example by the process of U.S. Pat. No. 4,401,829, by decomposition in the presence of merely catalytic quantities of alkali metal fluoride and in the absence of solvents, to give the corresponding perfluorodicarboxylic acid ester-fluorides, which, using ω-fluorosulfatoperfluorobutanoic acid ester as an example, can be represented in terms of formulae as follows:

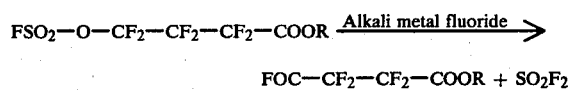

The corresponding perfluorinated vinyl ethers, which still have an ester group at the other end of the molecule, can then be prepared by the route outlined initially (reaction with hexafluoropropene epoxide, KOH/H$_2$O and scission of KF and CO$_2$) from the perfluoroalkane dicarboxylic acid fluoride-esters thus obtained. These vinyl ethers are—as mentioned initially—important monomers for the preparation of ion exchange compositions and the like.

Because of the simplicity of the starting materials and the procedure and because of the high degree of selectivity and product yield, the process according to the invention constitutes a considerable advance in this field. Compared with the methods possible hitherto, the process and the products of the process provide a simpler and more cost-effective access to, in particular, the industrially important perfluorinated vinyl ethers which still contain an ester group at the other end of the molecule.

The invention will now be exemplified in greater detail by means of the examples below, which illustrate the preferred embodiment of the process according to the invention (in an electrolytic cell).

EXAMPLE 1

The electrolytic cell comprises a laboratory-scale beaker glass cell 65 mm in diameter and 250 mm high, equipped with a cooling jacket. A magnetic stirring rod 30 mm in length and encased in PTFE (polytetrafluoroethylene) is located on the base of the vessel. A plate-shaped anode 55 mm wide and 3 mm thick, which is made of glassy carbon (Sigradur ®K, manufactured by Sigri Elektrographit GmbH, D-8901 Meitingen) and which is fastened to the lid of the cell, dips vertically into the vessel down to about 20 mm above the base. On both sides of the anode plate, and parallel to, and at a distance of approximately 25 mm from, the latter, there are platinum strips 10 mm wide, which are also fastened to the lid of the cell and act as the cathode. A gas inlet tube having an outlet orifice tapered to about 0.5 mm reaches down to 20 mm above the base of the cell. The device also has a solid carbon dioxide condenser, a thermometer and electrical connections to a source of direct current.

The electrolyte solution was prepared by adding 700 g of fluorosulfonic acid (technical grade, boiling point 60° C., $d_4^{20}$ 1.73) to 14.6 g (0.25 mole) of powdered sodium chloride, the bulk of the hydrogen chloride being evolved immediately. The solution was then flushed with dry nitrogen. A stream of approximately 5 l/hour of tetrafluoroethylene was then passed in, while stirring vigorously, and electrolysis was carried out for 10 hours at 8 amperes and at a temperature of 25°–35° C. In the course of this, the cell potential rose from 12 to 17 volts. When the electrolysis was complete, 340 g of liquid reaction products were separated off as the lower phase and the electrolyte phase was replenished with 160 g of fresh fluorosulfonic acid and it was re-used for the subsequent batch.

After a second batch had been put through, using the embodiment described above, it was possible to separate off 520 g of liquid reaction products. The electrolyte phase was replenished with 320 g of fresh fluorosulfonic acid. Three further batches were put through, recycling the electrolyte phase in each case, and gave the same results as the second batch.

The combined crude material discharged from the electrolysis (2,375 g) were subjected to a simple distillation at 100–10 mbar, in order to remove a small content of solid matter, and 2,310 g of distillate were obtained. The distillate was washed until it was neutral, first with water and then with sodium bicarbonate solution, and was then dried over a 4 Å molecular sieve. After drying, the crude product (2,000 g) had the following composition (area %) according to analysis by gas chromatography:

7.8% of FSO$_2$—O—CF$_2$—CF$_2$—O—SO$_2$F 76.0% of FSO$_2$—O—(CF$_2$—CF$_2$)$_2$—OSO$_2$F 12.9% of FSO$_2$—O—(CF$_2$—CF$_2$)$_3$—O—SO$_2$F 2.1% of FSO$_2$—O—(CF$_2$—CF$_2$)$_4$—O—SO$_2$F 0.5% of FSO$_2$—O—(CF$_2$—CF$_2$)$_5$—O—SO$_2$F.

The components in which n was 1, 2 and 3 were isolated and prepared in a pure state by fractional distillation of the mixture through a 1.2 m column packed with Raschig rings, 10 g of powdered calcium oxide being added. The following fractions were obtained:

| Fraction | Description | Quantity | Content according to GC (Area %) |
|---|---|---|---|
| bp below 105° C. | FSO$_2$—O—CF$_2$—CF$_2$—OSO$_2$F | 123 g | 89.4 |
| bp 105–137° C. | Intermediate runnings I | 115 g | — |
| bp 137–138° C. | FSO$_2$—O—(CF$_2$—CF$_2$)$_2$—O—SO$_2$F | 1,367 g | 99.8 |
| bp 138–168° C. | Intermediate runnings II | 70 g | — |
| bp 168–174° C. | FSO$_2$—O—(CF$_2$—CF$_2$)$_3$—OSO$_2$F | 176 g | 97.6 |

-continued

| Fraction | Description | Quantity | Content according to GC (Area %) |
|---|---|---|---|
| — | Residue | 137 g | — |

The components in which n was 4 and 5 were isolated and prepared in a pure state by fractional distillation of the combined residues (740 g) from several of of the distillations described above. The following fractions were obtained, using a 1 m Vigreux column under a pressure of 14 mbar:

| Fraction | Description | Quantity | Content according to GC (Area %) |
|---|---|---|---|
| bp/14 below 90° C. | First running | 109 g | — |
| bp/14 90–93° C. | $FSO_2-O-(CF_2-CF_2)_4-OSO_2F$ | 431 g | 96.9 |
| bp/14 94–115° C. | Intermediate runnings | 49 g | — |
| bp/14 115–117° C. | $FSO_2-O-(CF_2-CF_2)_5-O-SO_2F$* | 101 g | 96.8 |
| — | Residue | 47 g | — |
| $^{19}F$—NMR (CDCl$_3$): | $FSO_2-O-(CF_2-CF_2)_2-O-SO_2F$ | | |
| | + 50.9 (t, 2F, —O—SO$_2$F, Y = 8 Hz) | | |
| | − 83.4 (m, 4F, —O—CF$_2$—) | | |
| | − 125.0 (m, 4F, —CF$_2$—) | | |
| | $FSO_2-O-(CF_2-CF_2)_3-O-SO_2F$ | | |
| | + 50.9 (t, 2F, —O—SO$_2$F, Y = 8 Hz) | | |
| | − 83.2 (m, 4F, —O—CF$_2$) | | |
| | − 122.2 (m, 4F, —CF$_2$—) | | |
| | − 24.8 (m, 4F, —CF$_2$—) | | |
| | $FSO_2-O-(CF_2-CF_2)_4-O-SO_2F$ | | |
| | + 50.8 (t, 2F, —O—SO$_2$F, Y = 8Hz) | | |
| | − 83.4 (m, 4F, —O—CF$_2$—) | | |
| | − 122.2 (m, 4F, —CF$_2$—) | | |
| | − 124.9 (m, 8F, —CF$_2$—) | | |
| | $FSO_2-O-(CF_2-CF_2)_5-O-SO_2F$ | | |
| | + 50.6 (t, 2F, —O—SO$_2$F, Y = 8 Hz) | | |
| | − 83.5 (m, 4F, —O—CF$_2$—) | | |
| | − 122.2 (m, 4F, —CF$_2$—) | | |
| | − 125.0 (m, 12F, —CF$_2$—) | | |

*Melting point 39–40° C.

In all the batches of this example, the concentration of peroxodisulfuryl difluoride in the liquid electrolyte phase was approximately 0.06 mole/l in the initial phase of the first batch and about 0.015 mole/l in the further course of the reaction (method of determination: 2 ml of electrolyte were added to a solution of KI containing ice, and the iodine precipitated was determined with thiosulfate solution).

EXAMPLE 2

The electrolysis apparatus described in Example 1 was used.

The electrolyte was prepared by making up a solution composed of 37.2 g (0.5 mole) of potassium chloride and 750 g of fluorosulfonic acid, and removing the hydrogen chloride by blowing with nitrogen. A stream of gaseous hexafluoropropylene (approximately 7–9 l/hour) was passed in, while stirring, at such a rate that there was always an excess of hexafluoropropylene (reflux). Electrolysis was carried out at 8 amperes and at a temperature of 25°–35° C. until 68 ampere-hours had been passed. In the course of this the cell potential rose from 14 to 19 volts. When the electrolysis was complete, 520 g of organo-fluorine reaction products were separated off as the lower phase, and the electrolyte was replenished with 250 g of fresh fluorosulfonic acid and re-used for the subsequent batch. When 73 ampere-hours had been passed in the course of carrying out the second batch, 650 g of an organo-fluorine phase were separated off and the electrolyte was replenished with 280 g of fresh fluorosulfonic acid. 9,140 g of organo-fluorine reaction products were obtained after carrying out a total of 15 electrolysis batches, re-using the electrolyte phase.

The proportion, as determined by gas chromatography, of 2:1 adducts in the organo-fluorine reaction products averaged 84.5 area % in batches 1 to 5, 85.1 area % in batches 6 to 10 and 88.5 area % in batches 11 to 15.

The combined crude material discharged from the electrolysis in batches 1 to 5 (3,040 g) was washed several times with water and then with sodium bicarbonate solution and was dried over a 5 Å molecular sieve. After drying and adding 10 g of calcium oxide, the crude mixture (2,855 g) was separated into the following fractions by fractional distillation under a reduced pressure of 290 mbar through a 1.2 m column packed with Raschig rings:

| Fraction | Description | Quantity | Content (Area %) |
|---|---|---|---|
| bp/290 below 124° C. | First running | 360 g | — |
| bp/290 124–125° C. | $(FSO_2-O-CF_2-CF(CF_3))_2$ | 2.241 g | 71.4* |
| — | Residue | 176 g | — |

-continued

| Fraction | Description | Quantity | Content (Area %) |
|---|---|---|---|
| $^{19}$F NMR (CDCL$_3$): | $FSO_2-O-CF_2-CF(CF_3)-CF(CF_3)-CF_2-O-SO_2F$ Mixture of diastereomers<br>+ 51.0 (m, 4F, $-O-SO_2F-$)<br>− 69.0 (m, 6F, $-CF_3$)<br>− 69.5 (m, 6F, $-CF_3$)<br>− 73.0 (m, 4F, $-CF_2-$)<br>− 73.5 (m, 4F, $-CF_2-$)<br>− 176.0 (m, 4F, CF) | | |

*It was not possible to remove the other 2:1 adducts by fractional distillation. However, the by-products do not interfere with various subsequent reactions.

The concentration of peroxodisulfuryl difluoride in the liquid electrolyte phase was about 0.035 mole/l in the initial phase of the first batch and was about 0.012 mole/l in the further course of the reaction. (Determined as in Example 1).

I claim:

1. A method for making an alpha, omega-bis-fluorosulfatoperfluoroalkane which comprises introducing a perfluorinated alpha-olefin into a liquid phase containing peroxodisulfuryl difluoride at a substantially constant concentration of about 0.005 to 0.2 mole per liter.

2. A method as in claim 1 wherein said concentration of peroxodisulfuryl difluoride is about 0.01 to 0.1 mole per liter.

3. A method as in claim 1 wherein said perfluorinated alpha-olefin has the formula $$CF_2=CF-R_f,$$

wherein $R_f$ is F or perfluoroalkyl.

4. A method as in claim 3 wherein $R_f$ is perfluoroalkyl having 1 to 8 carbon atoms.

5. A method as in claim 3 wherein $R_f$ is $CF_3$.

6. A method as in claim 3 wherein $R_f$ is F.

7. A method as in claim 1 wherein said perfluorinated alpha-olefin is introduced into the liquid phase of an electrolytic cell wherein said peroxodisulfuryl difluoride is being generated.

8. A method as in claim 7 wherein said perfluorinated alpha-olefin has the formula $$CF_2=CF-R_f,$$

wherein $R_f$ is F or perfluoroalkyl.

9. A method as in claim 8 wherein $R_f$ is perfluoroalkyl having 1 to 8 carbon atoms.

10. A method as in claim 8 wherein $R_f$ is $CF_3$.

11. A method as in claim 8 wherein $R_f$ is F.